United States Patent [19]
Ohishi et al.

[11] Patent Number: 6,019,945
[45] Date of Patent: Feb. 1, 2000

[54] SAMPLE ANALYSIS SYSTEM

[75] Inventors: Tadashi Ohishi, Ibaraki-machi; Masaaki Hanawa; Susumu Kai, both of Hitachinaka; Hiroshi Mitsumaki, Mito; Hideyuki Yanami, Hitachinaka, all of Japan

[73] Assignee: Hitachi Ltd., Tokyo, Japan

[21] Appl. No.: 09/046,683

[22] Filed: Mar. 24, 1998

[30] Foreign Application Priority Data

Mar. 26, 1997 [JP] Japan ................................. 9-074157

[51] Int. Cl.[7] ................................................ G01N 35/02
[52] U.S. Cl. ............................... 422/65; 422/63; 436/43; 436/47; 436/48
[58] Field of Search .................... 422/63, 65, 67, 422/103, 104; 436/43, 47, 48

[56] References Cited

U.S. PATENT DOCUMENTS

| | | |
|---|---|---|
| 5,207,986 | 5/1993 | Kadota et al. ............................ 422/65 |
| 5,209,903 | 5/1993 | Kanamori et al. ....................... 422/65 |
| 5,362,648 | 11/1994 | Koreyasu et al. ....................... 436/48 |
| 5,380,488 | 1/1995 | Wakatake ................................ 422/65 |
| 5,623,415 | 4/1997 | O'Bryan et al. ....................... 364/478 |
| 5,876,670 | 3/1999 | Mitsumaki et al. ..................... 422/65 |
| 5,902,549 | 5/1999 | Mimura et al. . |

FOREIGN PATENT DOCUMENTS 7-92171  4/1995  Japan .

*Primary Examiner*—Long V. Le
*Attorney, Agent, or Firm*—Beall Law Offices

[57] ABSTRACT

A sample analysis system includes blood serum analysis units, blood plasma analysis units and urine analysis units which are arranged along a main conveyor line. The width size of each analysis unit on the side along the main conveyor line is the same. Each analysis unit can be removed integral with a sampling line and its rack transfer device from, the main conveyor line. Removed analysis units can be replaced by each other without changing the entry and exit positions for the sample rack. The conveyor line has the same number of line frame segments as the number of the analysis units.

6 Claims, 6 Drawing Sheets

SAMPLE ANALYSIS SYSTEM

BACKGROUND OF THE INVENTION

1. Field of the Invention

The present invention relates to a sample analysis system, and in particular, it relates to a sample analysis system provided with a plurality of analysis units which are disposed along a conveyor line for conveying holders which hold sample containers.

2. Description of the Prior Art

For the analysis of samples such as blood or urine, an analysis system is proposed which analyzes a plurality of analysis items using a plurality of analysis units which are arranged along a conveyer line. For example, JP-A 7-92171 discloses that a plurality of analysis units each having a different number of analysis process samples per unit time are arranged along its main conveyor line, and that a sub conveyor line is provided between the main conveyor line and each analysis unit.

JP-A 7-92171 discloses an analysis system in which a container having been read of its data from a bar-code label attached thereon at the entrance of a main conveyor line is conveyed, transferred to a subline associated with a corresponding analysis unit, then after sample processing, the container is returned from the subline to the main conveyor line. Then, the sequence of transfer of containers is controlled such that average processing time in each analysis unit becomes equal.

However, in the conventional analysis systems of the prior art described above, when each of its plurality of analysis units to be arranged is installed along the conveyor line, its position becomes fixed with respect to the conveyor line. Therefore, in such a case when the analysis units having been installed are required to be replaced by other analysis units having a different process mode, or when the number of analysis units needs to be increased in order to enhance its sample processing capability, there occurs a problem that the conveyor line must be fully replaced with a new one thereby involving an overall change in the architecture of the analysis system.

SUMMARY OF THE INVENTION

An object of the invention is to provide a sample analysis system which can easily replace its analysis units with other analysis units having a different processing mode without replacing its conveyor line.

Another object of the invention is to provide a sample analysis system which can easily change the length of the conveyor line in accordance with an increment or decrement of the number of analysis units required in the analysis system, with at least a portion of its original structure of the conveyor line remaining.

According to one aspect of the invention, a transfer mechanism is provided for transferring a sample container holder between the conveyor line and a sampling area formed in each analysis unit, the transfer mechanism is disposed respectively corresponding to each one of the plurality of analysis units, wherein at least two analysis units of the plurality of analysis units are arranged to differ from each other at least in one of the types of reagent supply means, the number of analysis items that can be analyzed therein, the number of tests that can be processed in a unit time, or the species of samples to be processed therein, and wherein the at least two analysis units described above have the same attachment mechanism or the same shape thereof with respect to the conveyor line.

According to another aspect of the invention, the conveyor line of the invention is comprised of: a combination frame which combines a plurality of line segments connected in series, each line segment having a width size which is substantially the same as the width size of each analysis unit; and a conveyor belt mounted rotatably around the combined frame for conveying the sample container holders, and wherein each of the plurality of analysis units is attached to a corresponding line segment frame having substantially the same width size.

According to a preferred embodiment of the invention, each of the plurality of analysis units is provided with a dedicated line having a sample pipetting position, and the transfer mechanism for transferring the sample container holder between the conveyor line and the dedicated line is attached to each analysis unit. When any analysis unit is removed from the conveyor line, the dedicated line and transfer mechanism associated thereto are removed from the conveyor line together with the analysis unit. Thereby, positioning activities associated with sample positioning in each analysis unit and transfer positioning between the conveyor line and the dedicated line can be simplified.

According to another preferred embodiment of the invention, each transfer mechanism is provided on at least two analysis units such that each position of each transfer mechanism coincides with each other with respect to the conveyor line when at least two analysis units are replaced with respect to the conveyor line. These at least two analysis units have the same width size as each other along the conveyor line.

According to still another preferred embodiment of the invention, the number of the plurality of line segment frames which constitute the combined frame of the conveyor line is the same as the number of the plurality of analysis units. The conveyor belt for conveying the holders is mounted rotatably around the whole area of the combined frame.

DESCRIPTION OF THE PREFERRED EMBODIMENTS

Figure 1:
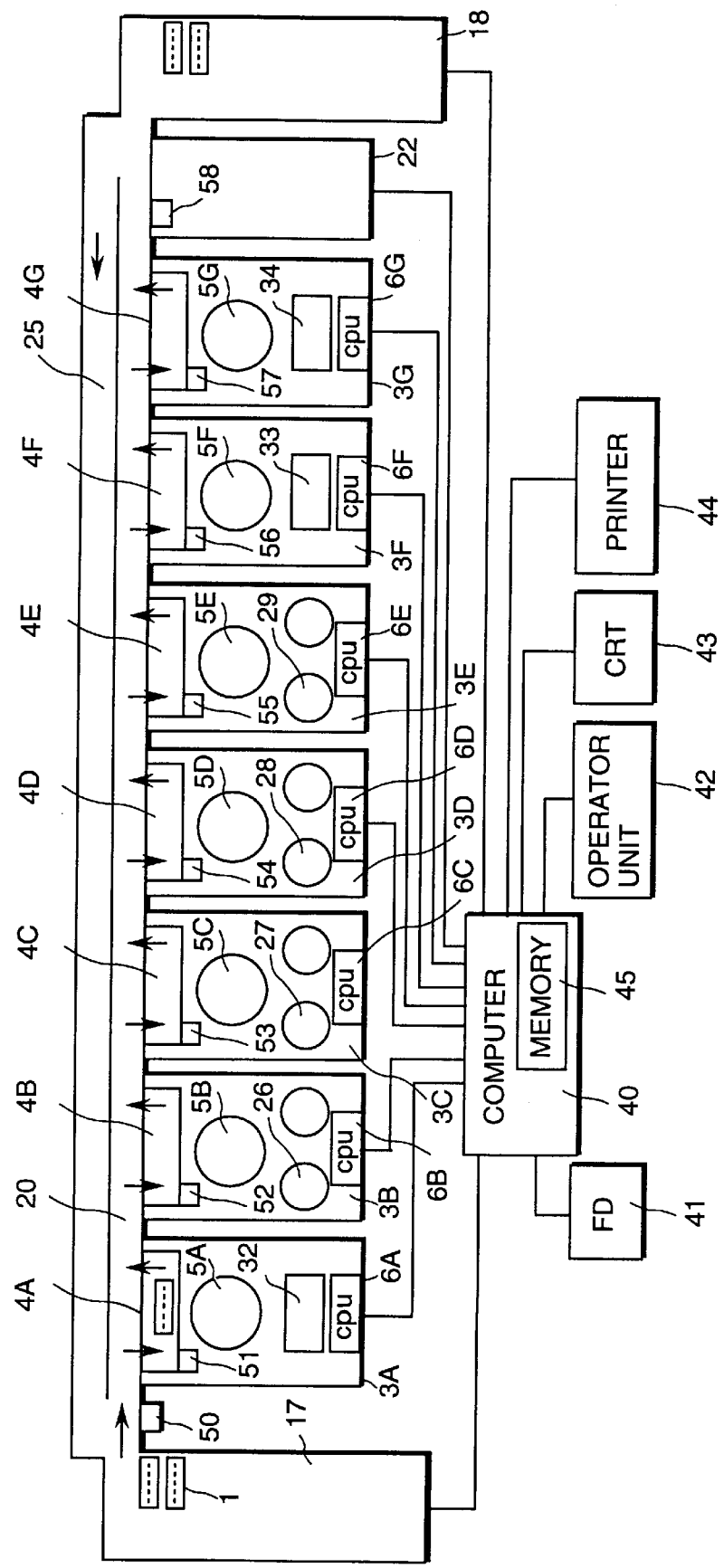
FIG. 1 is a schematic block diagram of a sample analysis system according to one embodiment of the invention.
Figure 2:
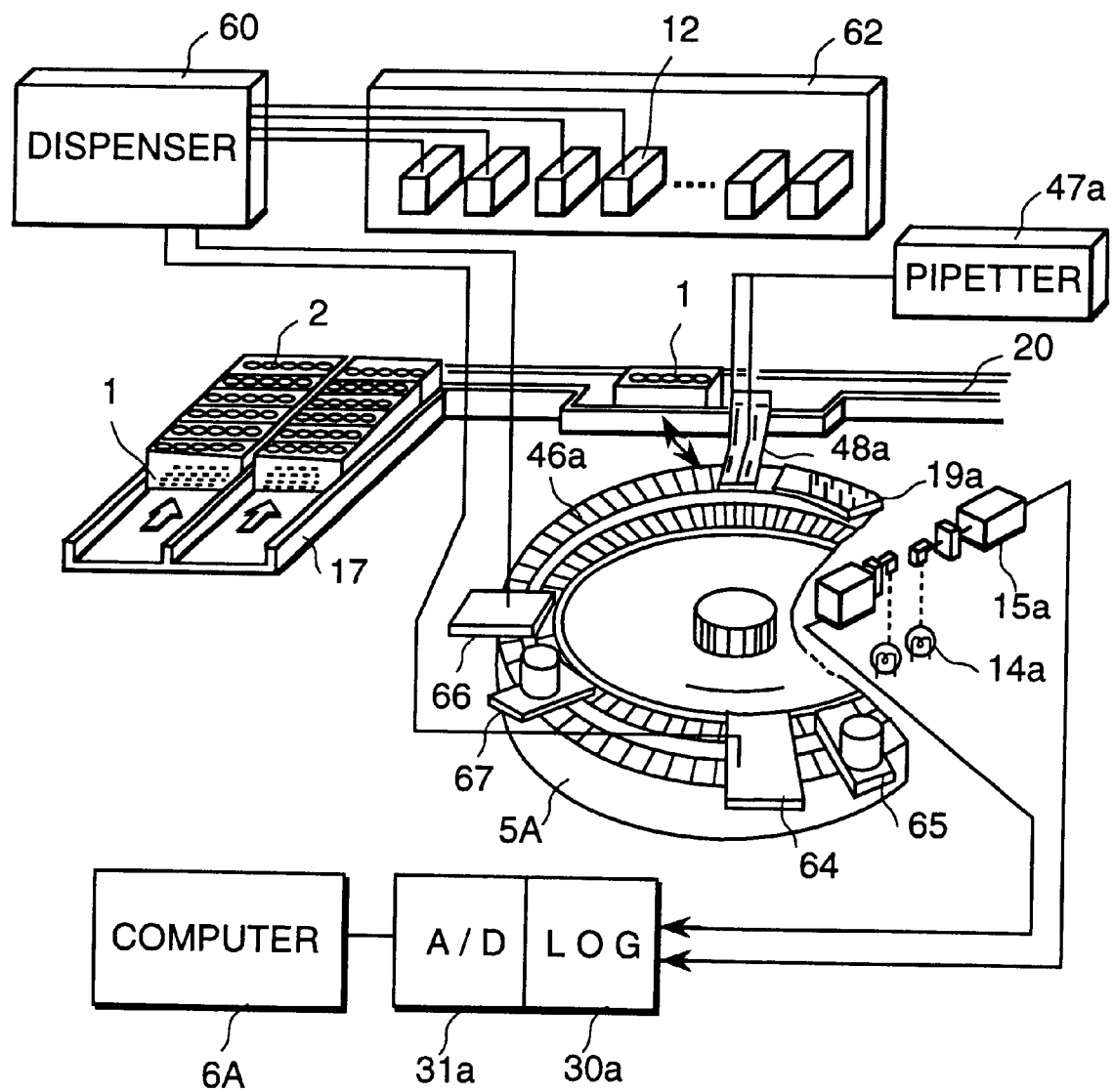
FIG. 2 is a schematic diagram indicative of an analysis unit provided with a dispenser type reagent supply section in the embodiment of FIG. 1.
Figure 3:
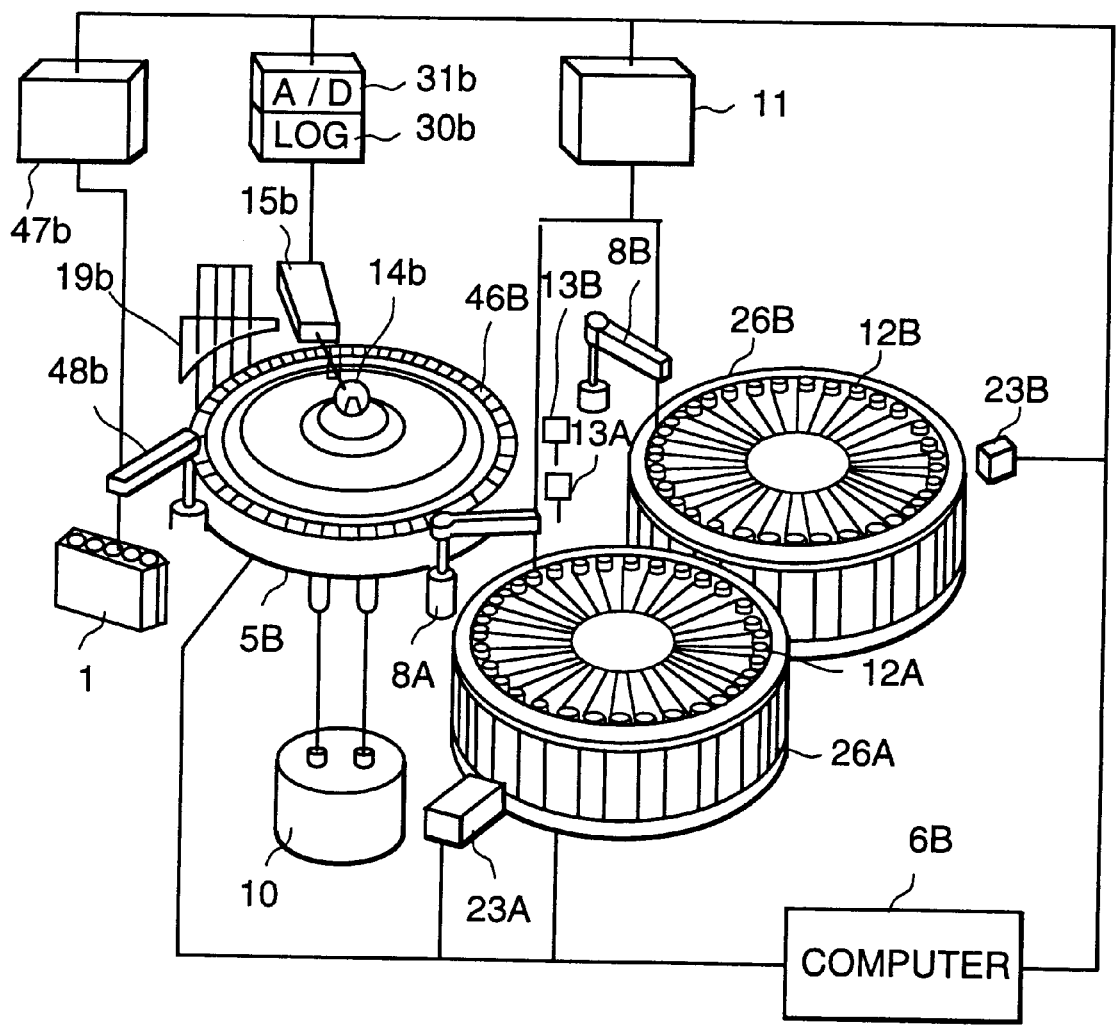
FIG. 3 is a schematic diagram indicative of an analysis unit provided with a pipette type reagent supply section in the embodiment of FIG. 1.

A preferred embodiment of the invention will be described with reference to FIGS. 1–7. FIG. 1 is a schematic block diagram of a multiple sample analysis system which can analyze multiple species of samples of blood serum, blood plasma and urine. The sample analysis system of FIG. 1 includes as its process unit one which uses a dispenser type reagent supply device as indicated in FIG. 2, and the other one which uses a pipetter type reagent supply device as indicated in FIG. 3 in combination. Other pretreatment devices such as a centrifugal separator, child sample pipetter and the like which are not directly involved in the analysis may be included as the process unit as well. In addition, an ion analysis apparatus using an ion selection electrode (ISE) can be the analysis unit. The sample analysis system of FIG. 1 is an example which does not include such pretreatment devices and ion analysis apparatus as its process unit. Analysis units 3A, 3F and 3G of FIG. 1 are a dispenser reagent supply type analysis unit having fixed analysis channels and dedicated pipette nozzles for each of a plurality of reagents. Analysis units 3B, 3C, 3D and 3E are a pipetter reagent supply type analysis unit in which analysis channels are not fixed thereby allowing random access, and a single reagent pipette nozzle is enabled to pipette appropriate reagents sequentially according to any specific analysis items.

In FIG. 1, analysis conditions of analysis units 3A, 3B and 3C are set to execute analysis processing of species of samples which are blood serum, those of analysis units 3D and 3E are set to execute analysis processing of species of samples which are blood plasma, and those of analysis units 3F and 3G are set to execute analysis processing of specimens of samples which are urine, respectively. Analysis units 3A to 3G are provided with a sampling line 4A to 4G, respectively which is a dedicated line which has a function to fetch sample rack 1 which is a holder of sample containers from main conveyor line 20, to move the rack to a sampling position, then to return it to the main conveyor line 20. Further, each analysis unit is installed corresponding to each sampling line 4A–4G, and is provided with: an ID information reader 51–57 which reads out ID information of sample rack 1 or ID information of each sample container carried by sample rack 1; a reaction section 5A–5G in which a reaction proceeds as specified in accordance with analysis items between the samples and reagents, and the result of reactions is optically measured; and reagent supply sections 26–29, 32–34. Numerals 26, 27, 28 and 29 of respective analysis units depict pipetter type reagent supply devices, and numerals 32, 33 and 34 depict dispenser type reagent supply devices.

At least two analysis units in the plurality of analysis units 3A–3G have the same width sizes as each other on the side thereof along main conveyor line 20. For example, analysis units 3A, 3B and 3C are arranged to have the same species of samples to analyze which is blood serum, and to have the same width size on their sides along the main conveyor line. In addition, sampling lines 4A, 4B, 4C provided in respective analysis units as a dedicated line for moving the sample container holder to its sample pipetting position have the same shape and size with each other. A transfer mechanism for transferring sample rack 1 which holds sample containers from one place to another between main conveyor line 20 and sampling lines 4A–4C of respective analysis units 3A–3C is attached to the side of each analysis unit.

When analysis units 3A, 3B and 3C are to be interchanged mutually apart from their original positions of installation, each analysis unit is removed from the main conveyor line integral with sampling line 4A–4C associated thereto and its transfer mechanism as mounted thereon, to be able to be installed in another place. In this case, since the positions of fitting structure and connecting parts of each analysis unit are the same with respect to main conveyor line 20, even if a different analysis unit is attached to the conveyor line in place of the removed one, positional relation of its transfer mechanism relative to the conveyor line is identical with that of the removed one. Therefore, the positions from which to transfer the sample container holder from the main conveyor line to each dedicated line, and from which to return the sample container holder from each dedicated line to the main conveyor line are invariable.

As will be described later, analysis units 3A–3C have a different number of analysis items that can be processed or a different type of reagent supply means from each other. In the sample analysis system of FIG. 1, all of the analysis units 3A–3G have the same outside dimensions, and the same attachment structure with respect to the conveyor line, thereby allowing any analysis unit to be interchanged at any position. However, these analysis units are arranged such that at least one of the reagent supply types, the number of analysis items that can be processed, the number of tests that can be processed per unit time, or the species of samples that can be processed differ from each other. A rack delivery portion 17 has an area sufficient to be able to set a plurality of sample racks 1 therein, and a delivery mechanism to deliver the plurality of sample racks 1 one by one to main conveyor line 20. A rack recovery portion 18 has an area to recover sample rack 1 which holds samples having been processed and analyzed in either of the plurality of analysis units, and an alignment mechanism to align the recovered sample racks in order. A temporary storage portion 22 stores sample rack 1 temporarily until the result of measurements of its samples having been sampled by any analysis unit is output, sends it back for reexamination via reexamination rack conveyor line 25 of main conveyor line 20 when it is required, and conveys the sample rack to rack recovery portion 18 when no reexamination is required.

A control unit has a host control computer 40, distributed control computers 6A–6G provided in respective analysis units for executing required processing and control therefor, and a floppy disk memory 41. Data processing of output signals from a photometer provided in each analysis unit is shared and executed by analysis unit's computers 6A–6G, and host control computer 40 connected thereto executes operation control of each analysis portion, the rack transfer system and other necessary portions in the system, and also executes arithmetic operations and control required for various information processing. Load sharing by computers, however, is not limited to the above, and can be modified to have various modes thereof according to necessity of architecture, or the distributed computers at each analysis unit can be eliminated by using only the host control computer 40. The host control computer 40 is provided with a memory portion 45, and is connected to an operator panel 42 for data entry, a CRT 43 for information display and a printer 44 for output of the result of measurements.

Sample rack 1 is a sample container holder having a box-like shape as depicted in FIG. 2 in which a plurality of sample containers 2, for example, in the number of five are loaded, respectively. However, its shape is not limited to the box, and any shape may be adopted. On an external surface of sample rack 1, an ID information record medium indicative of rack ID information is attached. On an external surface of each sample container 2, an ID information record medium indicative of its sample ID information is attached. As these ID information record mediums, a bar-code label, magnetic recording medium and the like are used. A bar-code attached on sample rack 1 has information regarding its rack serial number and sample species. A bar-code attached on each sample container 2 has information regarding its sample, for example, serial number, date of entry, name and entry number of patient, sample species, sample analysis items requested and the like.

ID information reader 50 provided in FIG. 1 reads ID information (on bar code) of sample rack 1 or sample container 2 before it is delivered by main conveyor line 20, and inputs its result to computer 40. Further, ID information reader 58 provided in temporary storage section 22 reads ID information from the bar-code on sample rack 1 or sample container 2 when they enter and exit from temporary storage section 22, and transmits its data to host computer 40.

Reagent bottles 12A, 12B for use in various items of analysis which are accommodated in a reagent supply section in each analysis unit 3A–3G have their reagent ID information on bar code or the like attached on their external surfaces. This reagent ID information includes reagent manufacture lot number, reagent bottle size, quantity of reagent that can be serviced, expiration date, sequential number which differs from bottle to bottle, analysis items and the like. Such reagent ID information is read by the bar code reader, and entered into memory section 45 associated with each corresponding analysis unit 3A–3G, as well as with the set position of its reagent bottle in the reagent supply section, available number of analysis remaining calculated from the initial quantity of solution and a unit dose, types of analysis items, serial number of the analysis unit accommodating the reagent, and the like.

Main conveyor line 20 which includes a conveyor belt for carrying sample rack 1 and a motor for driving the belt is controlled by the control unit to transport the sample rack continuously to a desired position. Each sampling line 4A–4G can move its conveyor belt intermittently so as to receive the sample rack at a rack entry position, stop it at a sampling position and at a rack exit position. In the example of FIG. 1, each sampling line is indicated to have the same form and the same size, and to be positioned at a predetermined place in each analysis unit. Sample rack 1 delivered by main conveyor line 20 is moved along a row of analysis units, stopped in front of a particular analysis unit designated by the control unit, and immediately transferred to a rack receive position on the sampling line of the designated analysis unit by its rack transfer mechanism (which will be described more in detail later). Sample rack 1 having completed sample pipetting operation at its sampling position is returned from the rack exit position on the sampling line to main conveyer line 20 by the rack transfer mechanism.

With reference to FIG. 2, an example of a configuration of an analysis unit having a dispenser type reagent supply system will be described. Reactor section 5A in analysis unit 3A is comprised of concentrically aligned two rows of reactors, each row including a plurality of transparent reactor, 46a, and a multi-wavelength photometer 15a provided for each row of reactors for analyzing spectroscopic multiwaves of light emitted from light source 14a and transmitted through reactor 46a. To serve each row of reactors, there are disposed in the vicinity of reactor section 5A a sample pipetter 48a having a pipette nozzle connected to sample pipetter pump 47a; a first reagent nozzle group holder portion 64 and a second reagent nozzle group holder portion 66 each connected to reagent dispenser pump 60; a first stirrer 65 and a second stirrer 67; and a reactor cleaning mechanism 19a. A reagent refrigerator 62 stores therein reagent bottles 12 of a first reagent and a second reagent for use in a plurality of analysis items (only for required analysis items), which are aligned therein and cooled at a predetermined low temperature. Each reagent solution in each reagent bottle is supplied via each tube and by reagent dispenser pump 60 to a corresponding reagent injection nozzle disposed over the rows of reactors. In this case, dispenser type reagent supply section 32 in analysis unit 3A of FIG. 2 includes reagent dispenser pump 60 of FIG. 2, reagent refrigerator 62 which cools the plurality of reagent bottles 12 therein, the first reagent nozzle group holder 64, the second reagent nozzle group holder 66 and the like.

Each sample rack 1 supplied from rack delivery portion 17 is conveyed by main conveyor line 20, and when any analysis by analysis unit 3A is required, sample rack 1 is transferred to sampling line 4A corresponding to the analysis unit 3A. A predetermined amount of a sample on sample rack 1 which arrives at its sampling position is aspirated using a pipette nozzle of sample pipetter 48a and is injected into reactor 46a. Into this reactor positioned at a predetermined position on the reactor rows, a reagent corresponding to a specified analysis item is injected to produce a reaction. After a predetermined period of time, a reacted solution in reactor 46a is subjected to measurement of its optical property using multi wavelength photometer 15a. An output signal from multi wavelength photometer 15a is processed by logarithm converter 30a and A/D converter under control of distributed computer 6A of the analysis unit, then it is transmitted to host control computer 40. Dispenser type analysis unit 3F and 3G have the same configuration as that of analysis unit 3A.

Now, with reference to FIG. 3, an example of configuration of an analysis unit having a pipette type reagent supply system will be described. Within reactors 46b disposed in array on reactor section 5B in analysis unit 3B, reactions are allowed to proceed between samples and reagents specified for particular analysis items. Sample rack 1 transferred from main conveyor line 20 to sampling line 4B (indicated in FIG. 1) is positioned at its sampling position thereon, where using a pipette nozzle of sample pipetter 48b, the sample is aspirated and a predetermined quantity of the sample is injected into reactor 46b. Sample pipetter 48b is provided with sample pipetter pump 47b. Reactor section 5B is kept at a constant temperature (for example, at 37° C.) by isothermal liquid supplied from an isothermal tank 10.

Pipetter type reagent supply unit 26 in FIG. 3 is provided with two reagent disks 26A and 26B for use of a first reagent and a second reagent. A plurality of reagent bottles 12A and 12B containing various reagents prepared for a number of analysis items have their reagent ID information indicated on a bar code attached on their external walls, respectively. After reagent bottles 12A and 12B are loaded on reagent disks 26A and 26B, reagent ID information of each reagent bottle is read by bar code readers 23A and 23B. The information having been read out is associated with the set position of its reagent bottle on the reagent disk, its corresponding analysis item, the analysis unit number to which its reagent bottle is set, and the like, then is entered into memory 45. Reagent pipetters 8A and 8B, each having a pipetter nozzle which is free to swivel and is movable vertically, are connected to reagent pipette pump 11.

The array of reactors 46b having been injected with samples is rotated. A predetermined amount of reagent is aspirated using reagent pipetter 8A from reagent bottle 12A which contains the first reagent and which is positioned at a reagent aspiration position corresponding to its analysis item, then its first reagent is injected into reactor 46b which is positioned at a reagent adding position. After their contents are stirred by stirrer 13A at a stirring position, the array of reactors is moved several times, then when reactor 46b arrives at a second reagent adding position, reagent pipetter 8B aspirates a reagent from reagent bottle 12B which is positioned at its reagent aspiration position corresponding to its analysis item and injects the aspirated reagent into the reactor. Then, the contents of the reactor are stirred by stirrer 13B. With rotation of the array of reactors, a light flux from light source 14b is admitted to pass through reactor 46b, and the light having passed through the reaction solution in reactor 46b is examined by multi wavelength photometer 15b. Output signals of wavelength corresponding to any designated analysis items are processed by logarithm converter 30 and A/D converter 31b which are controlled by analysis unit computer 6B, and digital signals obtained are transmitted to host control computer 40. Reactor 46b having completed its measurements is cleaned by cleaning mechanism 19b and is used for subsequent tests. Configurations of analysis units 3C, 3D and 3E are the same as that of analysis unit 3B.

Now, operation of the embodiment of FIG. 1 will be described in detail.

Before sample rack 1 is set in rack delivery section 17, each analysis item to be examined for each sample requested from the requester is entered from operator unit 42 into host control computer 40 by being associated with each sample number in advance. Information on analysis conditions designated for each analysis item is stored in floppy disk memory 41. Among these an analysis conditions, analysis item code consists of five digit numbers. Parameters of the analysis conditions to be used commonly between plural analysis units designated for the same analysis items include the wavelength of measurements in the photometer, sample pipetting quantity, calibration curve correction method, reference solution concentration, the number of bottles of reference solution, limit value for analysis value abnormality check, and the like. Parameters of the analysis conditions which are stored corresponding to each reagent bottle include the number of required reagents, for example, from the first to the fourth reagents, codes of reagent bottles consisting of 5 digit numbers, pipetting quantity of reagents, the number of tests available per bottle of reagents, and the like. Analysis conditions of analysis units 3A, 3B and 3C are set to accept blood serum samples, analysis units 3D and 3E to accept blood plasma samples, and analysis units 3F and 3G to accept urine samples, respectively. Acceptable simple species and their analysis unit numbers are registered in the host control computer.

At the same time when reagent bottles are loaded in the reagent supply sections in respective analysis units 3A–3G, reagent ID information of each reagent bottle is registered in host control computer 40 associated with its corresponding analysis unit serial number. In this case, the same reagents for use in analysis of particular analysis items specified for the same species are loaded in a plurality of analysis units in the same group which are designated to handle the same sample species. For example, in the case of blood serum samples, analysis units of 3A, 3B and 3C are regarded as in the same group, then reagent supply section 32 of analysis unit 3A is loaded, for example, with reagent bottles containing GOT and GPT which are hepatoscopy test items with many sample test requests, and bottles containing calcium, UA and BUN for emergency test items. Reagent supply section 26 of analysis unit 3B is loaded, for example, with reagent bottles containing GOT, GPT which are hepatoscopy test items, and other reagent bottles containing reagents for other analysis items the number of requests for which is not many. Then, reagent supply section 27 of analysis unit 3C is loaded with reagent bottles containing, for example, calcium, UA, BUN which are emergency test items, and other reagents for other analysis items the number of request for which is not many. Therefore, hepatoscopy test items can be examined by two analysis units of 3A and 3B, while emergency test items can be analyzed by two analysis units of 3A and 3C. What reagent for what analysis item is to be loaded in duplicate in which analysis unit is determined by the operator in consideration of actual conditions of laboratories in respective facilities.

When respective reagent bottles, 12, 12A, 12B are loaded in each reagent supply section, each reagent ID information thereof attached on each reagent bottle is read, then using each reagent bottle code as a key, the information having been entered as its analysis conditions parameters is retrieved, then respective data corresponding to this reagent bottle such as its analysis item, size of the bottle, the number of analysis tests available, set position of the reagent bottle and the like are associated with each other and entered into host control computer 40. At the same time, a maximum allowable number of analysis for the same sample species and for the same analysis item calculated on the basis of a total number of reagent bottles for the same analysis item loaded in the plurality of analysis units which allow analysis of the same species and the same analysis item is registered, and displayed on CRT 43 as required.

After respective reagents corresponding to respective analysis items required for each analysis unit have been loaded, prior to subjecting samples to analysis processing, calibration curve correction operation for each analysis unit is carried out for all analysis items which can be analyzed in each analysis unit. Since a calibration curve correction value differs depending on a difference of reagent bottles set in each analysis unit, results of calibration curve corrections obtained in each analysis unit for each analysis item are stored in memory 45 of host control computer 40. These results of correction are used in calculation of concentrations when any analysis item corresponding thereto is being analyzed in each analysis unit.

At the same time when one of the plurality of sample racks 1 placed on rack delivery section 17 is pushed out to main conveyor line 20, ID information of sample rack 1 or of sample container 2 is read by ID information reader 50. On the basis of the information having been read, any particular sample species on that sample rack 1 is discriminated by host control computer 40, then an appropriate analysis group having been preconditioned for that particular sample species is selected, then upon a subsequent judgment, one of the analysis units in the selected group is determined as a destination of that sample. For example, here, it is discriminated as a blood serum sample, then the group of analysis units including 3A, 3B and 3C is selected.

Further, upon reading of the sample ID information, the registration status of its sample number and analysis item are verified, and each analysis item designated to be measured for each sample on sample rack 1 is discriminated, then it is judged by host control computer 40 which one of analysis units 3A, 3B and 3C should proceed with which analysis item of which sample. In this case, host control computer 40 monitors the number of analysis items having been designated for each analysis unit to carry out and how long it will take until completion of its sampling. In particular, with respect to any particular analysis item which can be analyzed by a plurality of analysis units, it is judged which analysis unit is best to be assigned that analysis item in order to be most efficient. For example, with respect to GOT and GPT of particularly designated analysis items, it is judged that either of analysis units 3A and 3B have a minimum number of samples in queue to be processed at that time, then one of them which has a minimum wait time is designated as its analysis unit. According to a degree of busyness among a plurality of analysis units, a particular analysis unit is automatically designated to proceed with a particular analysis item designated. However, it is not limited to such automatic designation method, and it is possible also for the operator to enter any priority of use of respective analysis units for each analysis item via operator unit 42 in advance.

Sample rack 1 having samples to be subjected to particular analysis items and having been determined of its destination (for example, to analysis unit 3B) is transported to the designated analysis unit 3B by main conveyor line 20, and it stops in front of entrance to sampling line 4B of the analysis unit 3B. Then, sample rack 1 is transferred to sampling line 4B, moved to its sampling position, where a predetermined sample is aspirated by sample pipetter 48a to be injected into reactor 5B, then the sample rack is returned to main conveyor line 20. When there remains some analysis items to be analyzed for the samples on sample rack 1, sample rack 1 is conveyed further to analysis unit 3C by main conveytor line 20, transferred to sampling line 4C, and subjected to sample pipetting. Amounts of reagents remaining in respective reagent bottles for use of respective analysis items in each analysis unit are monitored by host control computer 40. As a method for monitoring the remaining amounts of reagents, a level gage attached to the reagent pipette nozzle may be used to detect the level of reagent liquid in the bottle every time the reagent is aspirated, or a subtraction method may be used which subtracts from a total allowable number of analysis tests every time of reagent pipetting. In any case of these methods, whether or not the amount of any reagent for use in the analysis of that particular analysis item runs short is decided by host control computer 40 which determines whether or not the remaining number of allowed tests of analysis has reached a predetermined value. The predetermined value in this case is set at a small number such as 0, 1, 2 or the like which indicates a remaining number of tests. Further, when, for example, GOT reagent in designated analysis unit 3B is judged to be in shortage, GOT analysis in analysis unit 3B is interrupted and a simultaneous switchover of GOT analysis processing to analysis unit 3A which has a plenty of GOT reagent remaining therein is enabled. Thereby, subsequent samples requiring GOT analysis are transferred to analysis unit 3A which is in the second priority order in the group of processing GOT analysis.

The control unit in the embodiment of FIG. 1 apprehends which of respective analysis items is designated to which analysis unit to carry out its analysis processing, and these data are stored in memory 45. Host control computer 40 stores information regarding which of respective analysis items is being processed by which analysis unit in its memory table, and displays the information edited in table on CRT 43 when requested from the operator.

In the apparatus of the embodiment of FIG. 1, the operator can instruct each of analysis units 3A–3G to start or stop its operation through keying via operator unit 42. On the basis of instructions from the operator unit, host control computer 40 controls operations such that sample rack 1 delivered from rack delivery portion 17 is transported by main conveyor line 20 to either one of appropriate analysis units other than the analysis unit which has been interrupted in its operation. In particular, in the time permit such as a night shift time when samples need to be analyzed in emergency but its frequency is not great, the overall system can be operated in such a manner, for example, that only analysis units 3C for blood serum testing and analysis unit 3G for urine testing are kept operating and all other analysis units are stopped their operation. In the time zone when the number of samples increases, other analysis units will resume their operation.

Further, in the system arrangement of the embodiment of FIG. 1, if any one of the analysis units fails, the failed analysis unit is removed integral with its associated rack transfer mechanism from the conveyor line for repair. Although, the sample analysis system is kept devoid of the failed analysis unit until completion of its repair, the conveyor line is ensured to maintain its operation without being affected by the removed analysis unit. Although the overall system capability to handle sample analysis may be lowered, since sample analysis processing can be handled continuously by the remaining analysis units and the conveyor line connected thereto, the worst case of the shutdown of the overall sample analysis system can be avoided.

Still further, in the system arrangement of the embodiment of FIG. 1, if abnormality arises in any of the analysis units causing it to be unable to continue its analysis operation, the control unit instructs another analysis unit to take over its analysis assignment and its sample rack to be delivered thereto. For example, by providing a plurality of reagents for use for a plurality of analysis items in duplicate in two analysis units 3B and 3C, analysis operation for the plurality of analysis items can be ensured to be continued without interruption.

Figure 4:
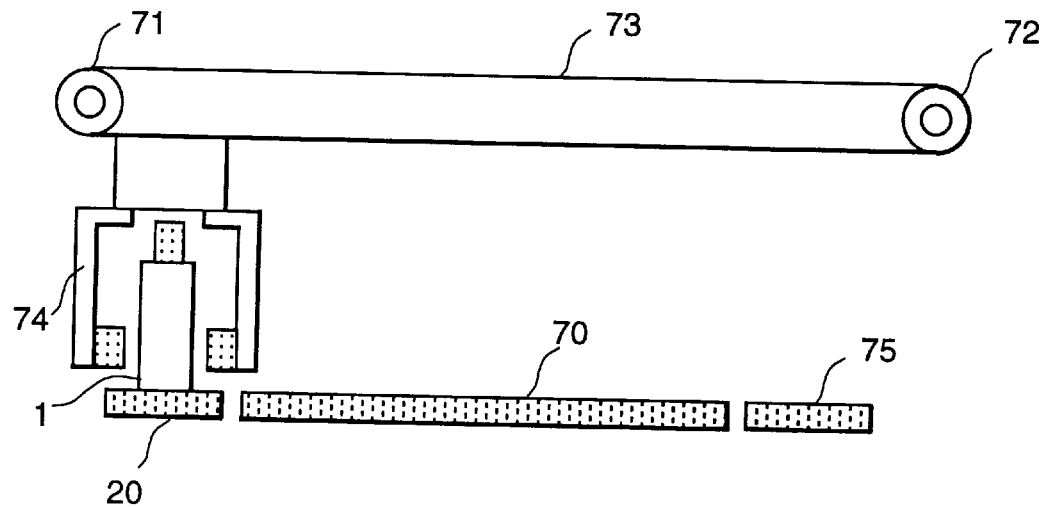
FIG. 4 is a schematic diagram indicative of a holder transfer mechanism in the embodiment of FIG. 1.

Now, with reference to FIG. 4, a rack transfer mechanism according to one embodiment of the invention is depicted. As such rack transfer mechanism, a traveling robot provided with a rack grip arm, a mechanism having a shove lever to shove a sample rack between the main conveyor line and the sampling line, and the like may be used. The example of FIG. 4 depicts one with a rack grip arm.

A communicating path 70 with a sufficient width to allow passage of sample rack 1 is provided between main conveyor line 20 and sampling line 75 (4A–4G in FIG. 1) on each analysis unit. The rack transfer mechanism is provided in the upper portion of communicating path 70, which includes primary pulley 71 attached to a motor drive axis, idler pulley 72, belt 73 wound around these pulleys, and gripper 74 having a pair of movable fingers and connected to belt 73. In FIG. 4, all of communicating path 70, sampling line 75, primary pulley 71 attached to the motor drive, idler pulley 72, belt 73 and gripper 74 are provided not on the side of the main conveyor line but on the side of each analysis unit.

The rack transfer mechanism which is disposed corresponding to each of the plurality of analysis units 3A–3G has the same shape and dimension. Directions of movement and drive timing of gripper 74 are controlled by the control unit. Since a position of attachment of any rack transfer mechanism to each analysis unit is the same for every analysis unit, when any two of these analysis units are replaced with each other, a relative position of the rack transfer mechanism before and after the replacement of respective analysis units is identical with respect to main conveyor line 20. Therefore, there occurs no problem in the transfer of the sample rack to and from respective analysis units even if at least two analysis units are exchanged.

The drawing of FIG. 4 indicates a state or the gripper 74 waiting on the main conveyor line for arrival of sample rack 1. From this state, gripper 74 seizes sample rack 1, and is moved by driving the motor via communicating path 70 to the position of sampling line 75, where sample rack 1 is freed from gripper 74 to be placed on sampling line 75. The reverse sequence of handling is executed when returning sample rack 1 from sampling line 75 to main conveyor line 20.

Main conveyor line 20 includes a conveyor belt to carry sample racks, a belt drive mechanism to drive the belt and a line frame to which the belt drive mechanism is attached. The line frame is comprised of a plurality of line segment frames in combination, and the number of the plurality of line segment frames which constitute the line frame normally coincides with the number of process units to be used. Namely, the number of analysis units as the process units may take any number, however, in the embodiment of FIG. 1, since the unit number from 3A to 3G is seven, the number of the line segment frames is set at 7. When the length of the main conveyor line is changed in accordance with the number of the line segment frames to be used, the conveyor belt of the main conveyor line is exchanged with another belt having a different length. Analysis units 3A–3G as the process units include an analysis section, a sampling line, and an analysis unit frame for mounting them, respectively. Each analysis unit frame is also provided with the rack transfer mechanism indicated in FIG. 4.

Figure 5:
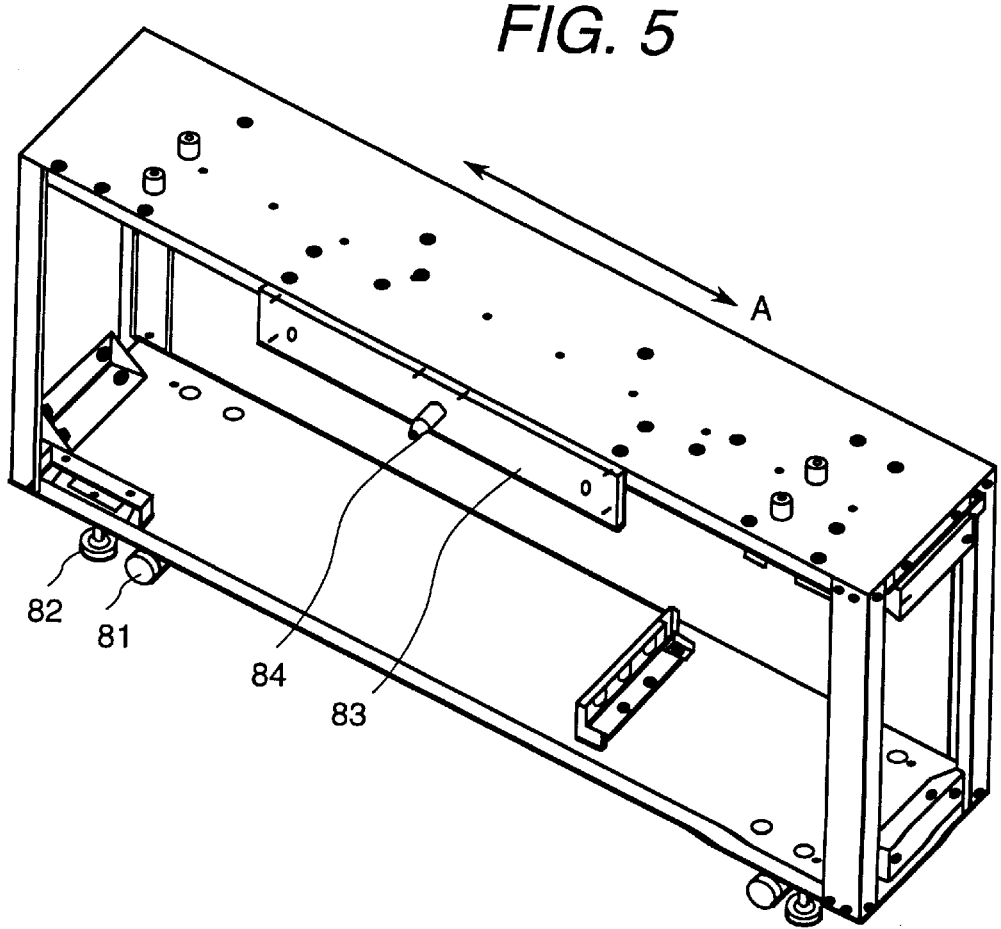
FIG. 5 is a perspective view of an example of a line segment frame for a main conveyor line in the embodiment of FIG. 1.
Figure 6:
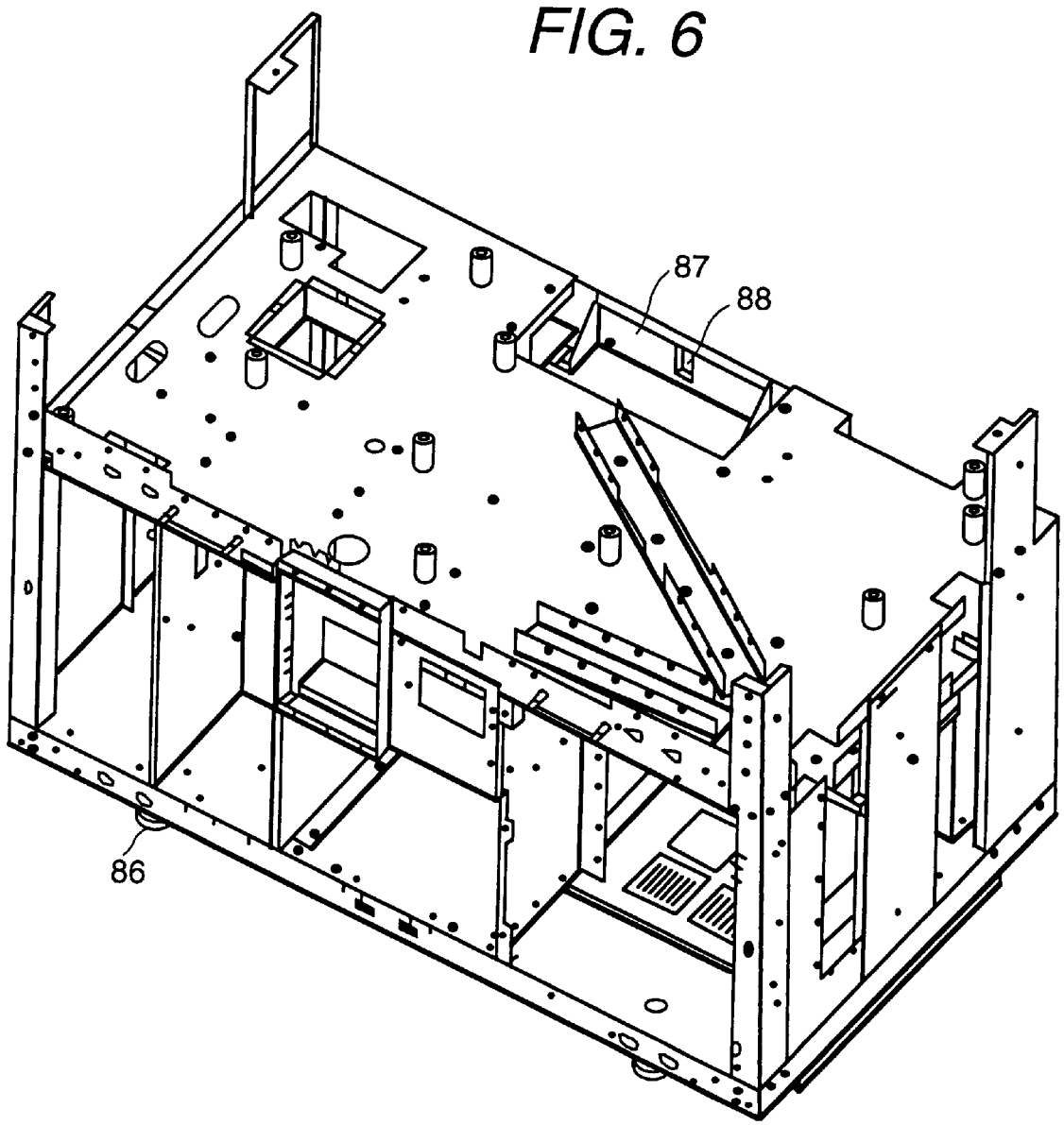
FIG. 6 is a perspective view of an example of an analysis unit frame in the embodiment of FIG. 1.
Figure 7:
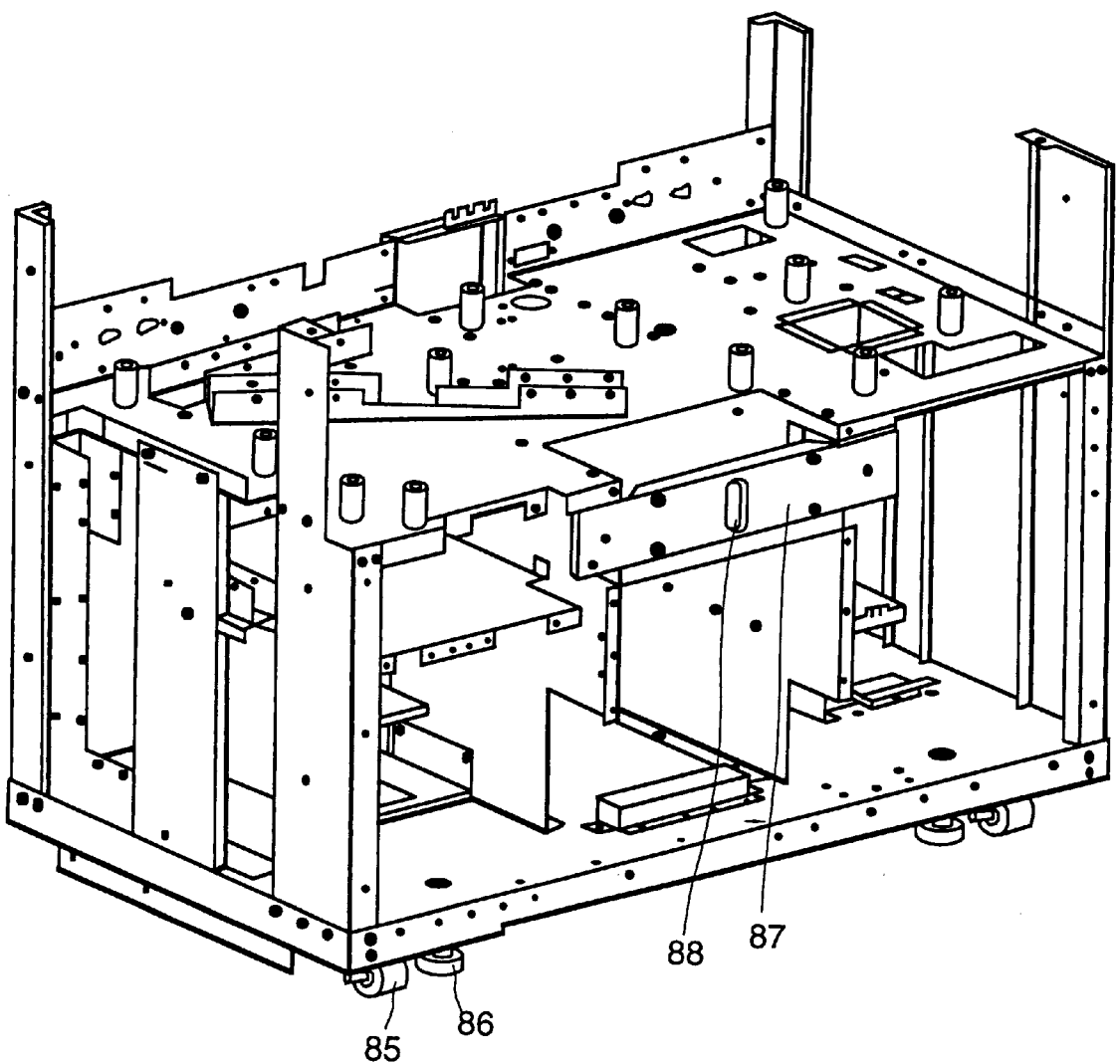
FIG. 7 is a perspective rear view of the analysis unit frame of FIG. 6.

FIG. 5 shows one line segment frame structure for use in main conveyor line 20. FIGS. 6 and 7 are perspective views of an analysis unit frame structure, FIG. 7 indicating a rear view of FIG. 6. In FIG. 5, the line segment frame is provided with casters 81 and position fixtures 82 on its bottom side. Position fixtures 82 are for fixing the frame at a preferred position. The line segment frame has a positioning panel 83 in the upper portion of its front side, and a positioning pin 84 in the center of the panel 83.

The line segment frame is provided corresponding to each one of analysis units 3A–3G. The conveyor line is constructed by connecting the same number of line segment frames in series in the directions of arrows as the number of total analysis units, and attaching a holder conveyor belt rotatably from one end to the other end over the full length of the combined frame. The combined frame is also provided with a belt drive mechanism. A width size of each line segment is slightly larger than a width size of each analysis unit corresponding thereto, but is substantially the same. Thereby, there exists no superfluous space between respective analysis units when they are installed.

The conveyor line constructed above is provided with two conveyor belts; one for the main conveyor line 20 and the other for reexamination rack conveyor line 25. To each line segment frame of the conveyor line, each of analysis units 3A–3G corresponding thereto is attached via positioning pin 84 in positioning panel 83. In the case of the embodiment of FIG. 1, the width size of all of the line segment frames corresponding to respective analysis units are the same, however, when any analysis unit which has a different width size is to be included, a line segment frame having a width size adaptable to that width size is combined.

Each of analysis units 3A–3G is attached to the conveyor line in a condition that all of its mechanical components including sampling line 4A–4G and rack transfer mechanism are installed. FIGS. 6 and 7 are given to help understand these attachment structure.

FIGS. 6 and 7 depict a skeleton framework of one analysis unit frame with all mechanisms removed. Each one of analysis units 3A–3G in the embodiment of FIG. 1 has the same frame as depicted in FIG. 6. The analysis unit frame is provided with casters 85 and position fixtures 86 on its bottom side. Position fixtures 86, like those of the line segment frame, are for fixing its frame at a preferred position when it is moved thereto. Its frame has a positioning panel 87 in the upper portion on the rear side thereof to engage with positioning panel 83 of the line segment frame, and a positioning hole 88 in the center portion of the panel 87 for allowing positioning pin 84 of the line segment frame to enter and engage. This engage hole has an oval shape extending vertically. By way of example, the expression of the front side and the rear side used here is only in relative meaning, however, in order to avoid any confusion, the rear side in FIG. 6 indicates the rear surface (in depth direction), and the front surface in FIG. 7. Positioning pin 84 in FIG. 5 and positioning hole 88 in FIG. 6 may be included in any of the line segment frame or the analysis unit frame.

Positioning hole 88 in the analysis unit frame provides a reference position to each analysis unit 3A–3G when attaching them to the conveyor line. The sampling line 41A–4G and rack transfer mechanism in any analysis unit are constructed to have the same distance from the reference position described above. When attaching the analysis unit to the conveyor line, positioning pin 84 of the line segment frame and oval hole 88 of the analysis unit frame are engaged with each other, then positioning panel 87 of the analysis unit frame is placed in close contact with positioning panel 83 of the line segment frame, and then both positioning panels are fastened with screws (not shown), thereby accomplishing connection therebetween.

Each analysis unit can be exchanged with each other with respect to the main conveyor line. This can be done easily by removing the screws which fasten between the positioning panel of a particular analysis unit to be exchanged and the positioning panel of the line segment frame to which the particular analysis unit is attached, separating the particular analysis unit from the line segment frame, and attaching the same to another line segment frame at a desired position in the same manner as described above. Further, the number of analysis units can be incremented or decremented. In this case, it is preferable for the number of the line segment frames which constitute the conveyor line to be incremented or decremented in accordance with the changes of the number of analysis units, and also for the belt of the conveyor line to be exchanged with another one having a length corresponding to a total length of the combined line segment frames. According to such embodiments as described above, sample analysis can be done flexibly in a manner corresponding to any number of samples to be analyzed, any number of analysis items and any species to be tested, thereby eliminating difficulty in the sample analysis operation or any substantial decrease in the analysis efficiency.

Positions of entrance and exit ports for the sample rack with respect to the main conveyor line are determined with reference to positioning pin 84 and which are the same with any analysis unit. That is, their entrance and exit are arranged in the same manner for each unit such that they coincide when analysis units are exchanged with one another. In addition, each width of each analysis unit on the side along the main conveyor line is the same with one another. This is not always necessary to be the same. However, if so, how differently the arrangement of the analysis units may have been modified, stop positions of the main conveyor line for transferring the sample rack to and from the sampling line can be set constant for every analysis unit, and also there results in no superfluous space in the direction of the main conveyor line.

All of the plurality of analysis units may be of the same type and configuration, or in which at least one of the reagent pipetting method, sample analysis processing capability, sample species, analysis method and the like may differ.

Each analysis unit has a sampling line as a dedicated conveyor line for its own use, and a distance between the main conveyor line and the sampling line is the same for every analysis unit. According to this arrangement, it becomes easy to specify a relative position between any sample container in any sample rack mounted on the sampling line and its sampling position. This is particularly important in the case of a trace sample analysis.

A locating distance of each analysis unit relative to the main conveyor line in the direction thereof is ensured by engagement of the positioning pin and the oval hole at a precise position, and a locating distance of each analysis unit relative to the main conveyor line in the directions of rotation thereof around a vertical axis which is perpendicular to the directions of the arrow and passes through the positioning pin is ensured precisely by a close contact and fastening with screws of the positioning panels of the main conveyor line and of the analysis unit. Further, the oval holes have a function to absorb any variation in heights of the main conveyor line and the analysis unit.

According to the features of the invention, it becomes possible to exchange analysis units having a different processing configuration and at a different location with respect to the main conveyor line while maintaining the main conveyor line ready to convey sample container holders (sample racks). Further, even if any one of the plurality of analysis units is removed from the conveyor line, sample container holders can be delivered to other remaining analysis units via the main conveyor line, thereby preventing interruption of the sample analysis handling. Still further, in compliance with the incrementing or decrementing of the number of analysis units installed in the analysis system, the length of the main conveyor line can be modified easily with at least a portion of the original structure of the main conveyor line remaining.

What is claimed is:

1. A sample analysis system having a conveyor line for conveying a holder which holds a plurality of sample containers; and a plurality of analysis units which are arranged along said conveyor line for carrying out analysis of a sample pipetted from said plurality of sample containers, comprising:

a transfer device disposed corresponding to each of said plurality of analysis units for transferring said holder between the conveyor line and a sampling area which is provided in each analysis unit, wherein, at least two of said plurality of analysis units have a structure which differs in at least one of a reagent supply type, an allowable number of analysis items that can be analyzed, an allowable number of tests that can be processed per unit time, and a type of species that can be processed;

said at least two of said plurality of analysis units have a same connection structure for connecting with said conveyor line; and wherein each said transfer device is connected to an analysis unit corresponding thereto so as to be removed integral with said analysis unit corresponding thereto which is removable from said conveyor line;

at least two transfer devices disposed corresponding to said at least two analysis units are connected to said at least two analysis units corresponding thereto in such a manner that when said at least two analysis units are exchanged in their positions relative to said conveyor line, a relative position of said at least two transfer device is the same with respect to the conveyor line with one another; and each of the at least two analysis units comprise a first positioning panel facing the side of the conveyer line, the conveyer line having second panels provided at a plurality of predetermined positions on the side thereof, each second panel being capable of engaging with the first panel of any of the analysis units.

2. A sample analysis system according to claim 1, wherein each said transfer device disposed corresponding to each of said plurality of analysis units has the same structure.

3. A sample analysis system according to claim 1, wherein said at least two analysis units have the same width on the side thereof along the conveyor line.

4. A sample analysis system having a conveyor line for conveying a holder which holds a plurality of sample containers; and a plurality of analysis units which are arranged along said conveyor line for carrying out an analysis of a sample pipetted from said plurality of sample containers, comprising:

a combined line frame including a plurality of line frame segments connected in series, the number of said plurality of line frame segments being the same as the number of said plurality of analysis units, wherein said conveyor line comprises a holder conveyor belt which is rotatably attached on said combined line frame;

each of said plurality of analysis units is connected to each of the plurality of line frame segments corresponding thereto;

said holder conveyor belt is rotatably to said combined line frame;

each of said plurality of analysis units comprises a dedicated line for moving the holder having been delivered from the conveyor line to a sample pipetting position therein;

said dedicated line is removable integral with an analysis unit corresponding thereto when said analysis unit is removed from the conveyor line; and wherein the sample analysis system further comprises a transfer device provided corresponding to each analysis unit for moving the holder between the conveyor line and the dedicated line, each analysis unit being separable from the conveyor line in a state where each analysis unit and the transfer device corresponding thereto is prevented from being separated from each other.

5. A sample analysis system according to claim 4, wherein each of said plurality of line frame segments which constitute said combined line frame has a width size which is substantially the same as a width size of an analysis unit corresponding thereto.

6. A sample analysis system according to claim 4, wherein each of said plurality of analysis units have the same width size on the side thereof along said conveyor line.

* * * * *